Figures 1, 2:
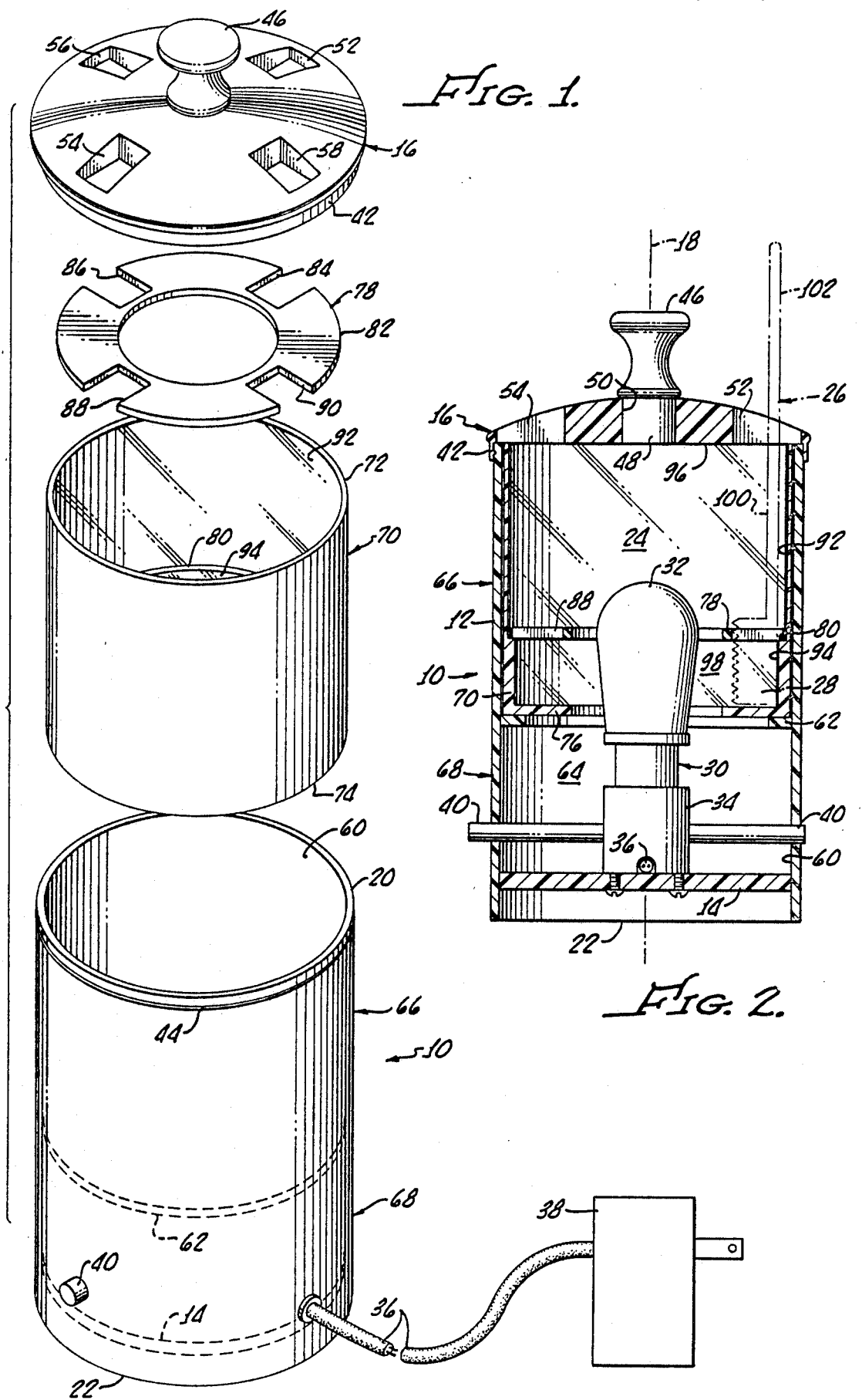

United States Patent [19]

Hylton et al.

[11] Patent Number: 4,806,770
[45] Date of Patent: Feb. 21, 1989

[54] GERMICIDAL TOOTHBRUSH HOLDER

[75] Inventors: William M. Hylton, 12871 Brittany Woods Dr., Santa Ana, Calif. 92705; John M. Zabsky; Virgil E. Littleton, both of Santa Ana, Calif.

[73] Assignee: William M. Hylton, Santa Ana, Calif.

[21] Appl. No.: 10,183

[22] Filed: Feb. 2, 1987

[51] Int. Cl.⁴ .............................................. G01N 23/00
[52] U.S. Cl. ................................ 250/455.1; 250/454.1
[58] Field of Search ............... 250/453.1, 454.1, 455.1, 250/492.1; 422/24, 300, 291

[56] References Cited

U.S. PATENT DOCUMENTS

| | | | |
|---|---|---|---|
| 2,592,131 | 4/1952 | Farrar | 250/455.1 |
| 3,100,842 | 8/1963 | Tellefsen | 250/455.1 |
| 3,114,038 | 12/1963 | Meader | 250/454.1 |
| 3,309,159 | 3/1967 | Le Sueur et al. | 250/454.1 |
| 3,820,251 | 6/1974 | Abernathy | 250/455.1 |
| 3,954,407 | 5/1976 | Andary et al. | 250/455.1 |
| 4,088,455 | 5/1978 | Ellis | 250/455.1 |

Primary Examiner—Bruce C. Anderson
Attorney, Agent, or Firm—Allan R. Fowler

[57] ABSTRACT

A germicidal toothbrush holder includes a substantially closed, upright cylindrical housing having a detachable top lid. The lid has an annular array of openings through which the bristled ends of toothbrushes may be inserted and removed. A UV lamp of low intensity is operably mounted within the housing for emitting ultraviolet radiation in the 200 to 300 nanometer wavelength range, as well as some radiation in the visible range above 300 nanometers and in the ozone producing range below 200 nanometers. A removable cup structure supports the bristled ends of the toothbrushes in an annular array immediately surrounding the lamp, and has an annular interior surface coated with aluminum for high reflectance of UV radiation. The UV lamp is on continuously to expose the toothbrushes to germicidal radiation and to generate small quantities of ozone which accumulate to have some sterilizing effect. The lower portion of the housing is translucent to visible light, so that the holder operates as well as a nightlight for the bathroom.

9 Claims, 1 Drawing Sheet

U.S. Patent    Feb. 21, 1989    4,806,770

GERMICIDAL TOOTHBRUSH HOLDER

This invention relates to toothbrush holders, and more specifically has reference to toothbrush holders which incorporate a germicidal or sterilization means for reducing the possibility of infection or reinfection among one or more family members utilizing a common toothbrush holder.

Ultraviolet light (UV) particularly in the 200 to 300 nanometer wavelength range has long been known for its germicidal and sterilization effects achieved by direct radiation. This has been attributed to its destructive effects on DNA and consequent destruction of the microorganisms. The 200 to 300 nanometer wavelength range is sometimes referred to as the "germicidal" or short wave ultraviolet band. Ultraviolet lamp bulbs used for germicidal purposes emit substantial UV radiation in this wavelength band, as well as typically some electromagnetic radiation in adjacent portions of the spectrum including the visible.

Also, UV radiation, especially that below 200 nanometers in wavelength, is known to produce small quantities of ozone from oxygen in the atmosphere. Ozone is a powerful oxidizing agent, and in sufficient concentration is known to have significant germicidal and sterilization effects.

One known method for sterilizing one or more articles in a holder is to immerse the same in a liquid germicidal bath. If properly implemented and maintained, the common germicidal bath may be scientifically effective; however, this method is not particularly appealing or suitable in the home environment.

As a practical matter, a toothbrush holder for the home should be small, inviting, rugged and handily used, with a minimum maintenance requirement and with the toothbrushes of different members of the family separated physically. It should be easily attached to a bathroom structure or conveniently accommodated on the limited area surrounding the bathroom sink or other nearby open shelf space.

These practical requirements probably account for the majority of homes where the typical toothbrush holder is an open rack, or a water glass or the like. Such holders themselves can become contaminated with infectious microorganisms either directly from the toothbrushes or otherwise; the multiple toothbrushes can come in contact with one another or with the same or different portions of the holder; and often, neither the holder nor the toothbrushes dry out between use. These factors enhance the living environment for and transmission of germs, therefore enhance the probability of infection and reinfection of the family members utilizing the toothbrush holder.

So far as is known, there has existed for some time a public need for an effective germicidal toothbrush holder in the form of a safe and practical home appliance suitable for the bathroom environment. The present invention, which utilizes the properties of UV radiation, is believed to be a significant advance toward filling that need.

In accordance with the present invention, a germicidal toothbrush holder is provided for receiving and holding a plurality of toothbrushes of the common type having an elongated handle with bristles disposed at the distal end thereof. The holder includes a hollow housing which encompasses an interior volume of space for receiving at least the bristle ends of the toothbrushes, and has means defining interior surfaces within the housing which immediately encompasses said space volume. An electric lamp is operably mounted interiorly of the housing, and has a ultraviolet light bulb which extends proximate to or within said space volume. The bulb emits an ultraviolet light spectrum which includes substantial radiation in the germicidal wavelength band. The bristle ends of said toothbrushes are supported within said space volume at spaced apart locations disposed proximate to the lamp bulb and to the interior surfaces encompassing the space volume, and means are provided for ingress and egress of the toothbrushes to and from the housing.

In accordance with one embodiment of the invention, the housing is upright and substantially closed by a detachable top lid. The top lid has a plurality of openings for providing ingress and egress of the bristled ends of the toothbrushes to and from the housing. The bristled ends of the toothbrushes are supported in an annular array immediately surrounding the lamp for direct irradiation thereby, and the vertical spacing between this supported position and the top lid is sufficient so that substantial portions of the toothbrush handles extend within the housing for direct irradiation along with the bristled ends, with the opposite or distal end portions of the handles protruding through the openings in the top lid for easy access without requiring removal of the lid.

The upright structure permits good use of gravity in supporting the toothbrushes while providing a convenient access through the lid openings. The spacing which incorporates a good portion of the toothbrush handles for irradiation, takes into consideration that such portion on the handle frequently is inserted into the users mouth when using the toothbrush and therefor should be sterilized.

Because of the close proximity of the bristled ends of the toothbrushes to the ultraviolet lamp bulb, and considering that the irradiation is continuous during the period of non-use of the toothbrushes, a low intensity lamp can be used. Moreover, by using surrounding interior surfaces comprised of a material selected to be highly reflective of ulraviolet radiation in the germicidal wavelength range, such as aluminum, the multiple reflections produced not only impinge on the toothbrushes from many directions to directly irradiate germs, but also optimize the direct application of the energy in the ultraviolet field thereby further diminishing the intensity requirement for the ultraviolet bulb. Considering that the bulb should operate continuously 24 hours a day, the wattage rating of the bulb required is significant. We have found a four watt bulb to be satisfactory. Although higher wattage bulbs may be used, low intensity bulbs insure safety especially for children who may remove the top lid and peer inside.

In a preferred embodiment of the invention, the annular interior reflective surface is provided by a cylindrical cup removably supported within the housing in surrounding coaxial relationship with the lamp bulb. The cup also provides the means for supporting the bristled ends of the toothbrushes by virtue of having an inwardly extending annular ledge formed adjacent its bottom end on which the bristled ends of the toothbrushes rest. Separation of the bristled ends of the toothbrushes is provided by a second inwardly extending annular ledge supported by the cup at a position above the first ledge. For this purpose, the second annular ledge has a plurality of openings therein disposed at spaced apart locations through which the bristled ends of the toothbrushes may be inserted to rest on the first or lower ledge in an annular array surrounding the ultraviolet lamp.

While the surrounding interior surface of the housing itself could be coated or lined with ultraviolet reflective material, the cup structure is preferred for defining this surface because the cup is conveniently removable to be cleaned.

Further, in the preferred embodiment of the invention, an ultraviolet lamp is employed which also radiates some energy at wavelengths in the visible spectrum as well as wavelengths that produce ozone from oxygen in the atmosphere. This permits the lower portion of the housing to be constructed of a translucent material, such as polypropolene plastic, and therefor to serve as an effective nightlight in the bathroom. While only small amounts of ozone are generated, the substantially closed housing tends to concentrate the ozone, thus taking some advantage of its germicidal effect in sterilizing the toothbrushes.

The small amount of heat generated by the ulraviolet lamp and the ventilated top lid of the housing assist in drying out the toothbrushes. Also, the detachable lid and removable cup permit access for cleaning the housing interior and for replacing the lamp bulb.

The above and other important features of the present invention will be better understood from the following detailed description of a preferred embodiment of the invention, made with reference to the accompanying drawings, in which:

FIG. 1 is an exploded perspective view of the germicidal toothbrush holder, generally illustrating the removal of the cup structure and detachable top lid from the housing; and, FIG. 2 is a cross-sectional elevation of the germicidal toothbrush holder in assembled form, and illustrating the position of a common toothbrush in phantom line.

Referring now to the drawings, the toothbrush holder 10 includes side and bottom walls 12, 14 and a detachable lid 16, all made of polypropolene plastic material which is translucent in the visible region but is absorptive of ultraviolet light. The side wall 12 is a substantially hollow right circular cylinder having a central longitudinal axis 18 and upper and lower edges 20, 22. The detachable lid, side wall and bottom wall form a substantially closed, upright housing of suitable compact construction to be movably placed in the usual limited area surrounding a bathroom sink, with the housing resting on the bottom circular edge 22 of the side wall.

The housing encompasses an interior volume 24 for receiving the bristle ends of a plurality of toothbrushes of the common type. The typical common toothbrush as shown in phantom line has an elongated handle 26 with bristles 28 disposed at the distal end thereof.

An electric lamp 30 having a bulb 32 for emitting ultraviolet light is removably mounted in a light socket 34, which is in turn centrally fixed to the bottom wall 14 of the housing. An electrical cord 36 extends from the electrical socket 34, through the side wall 12 of the housing, and thence to a power supply 38 adapted to be plugged into a common electrical outlet (not shown) as is found adjacent the sink area in most bathrooms. The electrical socket has an extended switch handle 40 which extends through opposite sides of the cylindrical side wall 12, for manual actuation to turn the ultraviolet light on and off. Together, the socket 34 extended switch handle 40 and electrical cord 36 constitute means for operatively mounting the lamp coaxially within the housing, with the lamp bulb 32 extended to within the space volume 24.

The top lid 16 is generally circular and has a depending annular skirt 42 which slips over the top edge 20 of the cylindrical side wall 12. The skirt 42 has an interior protrusion (not clearly shown) of v-shaped cross-section which snap-fits into a corresponding annular groove 44 formed on the side wall, with the protrusion and groove cooperating as a conventional detent mechanism for detachably securing the lid 16 to the housing. Mounted atop the lid is a knob 46 for facilitating the manual attachment and detachment of the lid, the knob being secured by an extension 48 thereof cemented or otherwise secured in a central opening 50 of the lid.

The lid 16 has a plurality of rectangular openings 52, 54, 56, 58 therein through which the bristled ends (typically shown at 28) of a plurality of toothbrushes may be respectively inserted into and removed from the housing. These openings are disposed at spaced apart locations in an annular array about the lid, and are of minimum size and shape to accommodate passage of the bristled ends of common toothbrushes.

The bottom wall 14 of the housing is a circular plate fixed to the interior surface 60 of the cylindrical side wall 12 of the housing near the bottom edge 22 thereof by any conventional means, such as cementing.

An annular ring 62 is similarly fixed to the interior surface 60 of the cylindrical side wall 12 of the housing, and serves as the abutment which generally divides the housing into the upper interior space volume 24 for receiving the toothbrushes, and a lower interior space volume 64 in which the socket 34 is disposed for removably mounting the lamp 30. Also, the ring 62 effectively divides the cylindrical side wall 12 into an upper portion 66 which encompasses the upper space volume 24, and a lower portion 68 which essentially encompasses the lower space volume 64.

A cylindrical cup structure 70 having top and bottom ends 72, 74, is removably supported within the housing by virtue of the bottom end 74 thereof abutting the internal fixed ring 62 and with the upper end 72 thereof being coterminous with the upper edge 20 of the cylindrical side wall 12. A first inwardly extending ledge 76 is formed at the bottom end of the cup, and a second inwardly extending annular plate or ledge 78 is removably supported within the cup by an annular abutment 80 formed interiorly of the cup at a location spaced above the first or lower annular ledge 76. The second or upper plate 78 has an outer annular periphery 82 which fits in close engagement with the interior of the cup 70, and which is interupted by a plurality of openings 84, 86, 88, 90 therethrough disposed in overlying relationship to the annular ledge 76 formed at the bottom of the cup and registering with the lid openings.

But for the bottom ledge 76, the interior of the annular cup is comprised of two cylindrical surfaces 92, 94 separated by the small abutment 80, and generally constituting overall a cylindrical surface which immediately encompasses the upper space volume 24. These surfaces, 92, 94, as well as the bottom surface 96 of the removable lid, are coated or lined with aluminum or aluminum alloy, and are highly reflective of ultraviolet radiation particularly in the germicidal range.

As seen from FIG. 2, the bulb 32 of the ulraviolet lamp extends upwardly and centrally into the upper space volume 24, thereby, in conjunction principally with the reflective interior annular surface 94 of the cup, defining a lower annular portion 98 of the upper space volume 24.

The bristle end of each of the plurality of toothbrushes (typified by the bristle end 28 of toothbrush 26 in phantom) may be inserted through the annular array of openings in the top lid thence through the openings in the upper ledge or plate 78 to rest on the lower annular ledge 76 of the cup, resulting in an annular array of vertically oriented toothbrushes supported with bristle ends downwardly at spaced apart locations in the annular portion 98 of the upper space volume 24, thus immediately surrounding the lamp bulb 32 for direct and proximate irradiation.

The vertical spacing between the lower ledge 76 of the cup and the top lid 16 is sufficient to include substantial portions of the toothbrush handles within the space volume 24 for direct irradiation by the lamp 30, while permitting opposite end portions of the handles to protrude from the top lid. See, for example, the corresponding includes portion 100 and protruding portion 102 of the toothbrush handle 26.

Since the upper portion 66 of the cylindrical side wall 12 is blocked by the reflective surfaces of the cup, visible light generated by the bulb 32 will emerge principally through the translucent bottom portion 68 of the side wall, and through unblocked portions of the openings in the lid, the bottom surface of which is also reflective. The emergence of the visible light enables the holder to function as a nightlight.

The UV bulb 32 may be a low intensity bulb operating at about four watts from the power supply 38, which supplies limited and safe low voltage electrical power to the socket 34 not substantially in excess of that conventionally required to operate the bulb 32. Low intensity bulbs also are a safety factor in the event a child should remove the top lid, thus exposing the child to direct ultraviolet radiation. We have utilized a UV bulb No. 0Z4S11 from American Ultraviolet Company of Santa Ana, Calif.

In use, the lid 16 is not normally removed. Rather, toothbrushes are inserted and removed through the openings in the lid as required by grasping their protruding handle portions. The lid, however, may be removed in order to remove the cup 70 and upper ledge or plate 78 for cleaning, or to gain access to the housing interior for any purpose including cleaning or bulb replacement. As with the side wall 12, the cup 70 and upper ledge or plate 78 are made of polyproplene material.

What is claimed is:

1. A germicidal toothbrush holder for receiving and holding a plurality of toothbrushes of the common type having an elongated handle with bristles disposed at the distal end of the handle, said germicidal toothbrush holder comprising:
   (a) a substantially hollow, upright, cylindrical housing having a vertical axis;
   (b) said housing comprising bottom and side walls and a detachable top lid, all approximately centered on the vertical axis and together encompassing an interior volume of space including an upper space volume for receiving at least the bristled ends of said toothbrushes, and a lower space volume;
   (c) means disposed in said upper space volume for defining a cylindrical interior surface within the housing, which surface immediately encompasses said upper space volume, and is reflective of radiation in the 200–300 nanometer wavelength spectrum;
   (d) an electric lamp having a bulb for emitting ultraviolet light which includes substantial radiation in the 200 to 300 nanometer wavelength spectrum;
   (e) means for mounting the lamp operably within the housing adjacent the bottom wall thereof, with the lamp bulb extending upwardly to within said upper space volume;
   (f) said lamp bulb being disposed approximately coaxially with the housing, and being spaced apart from said cylindrical interior surface so as to define an annular portion of said upper space volume therebetween; and,
   (g) means for supporting the toothbrushes in vertical orientation, with the bristled ends downward and disposed at spaced apart locations surrounding said lamp within the annular portion of said upper space volume;
   (h) said supporting means comprising:
      means defining a first inwardly extending annular ledge disposed in said upper space volume for abutting the bristled ends of said toothbrushes; and,
      means defining a second inwardly extending annular ledge disposed in said upper space volume at a location spaced above said first annular ledge, said second annular ledge having a plurality of openings therein disposed at spaced apart locations through which the bristled ends of said toothbrushes may be inserted respectively to rest upon said first annular ledge.

2. A germicidal toothbrush holder, for receiving and holding a plurality of toothbrushes of the common type having an elongated handle with bristles disposed at the distal end of the handle, said germicidal toothbrush holder comprising:
   (a) a substantially hollow, upright housing having a vertical axis;
   (b) said housing comprising bottom and side walls and a detachable top lid, all approximately centered on the vertical axis and together encompassing an interior volume of space for receiving at least the bristled ends of said toothbrushes;
   (c) means defining an annular interior surface within the housing, which surface immediately encompasses said space volume;
   (d) an electric lamp having a bulb for emitting ultraviolet light which includes substantial radiation in the 200 to 300 nanometer wavelength spectrum;
   (e) means for mounting the lamp operably within the housing adjacent the bottom wall thereof, with the lamp bulb extending upwardly to within said space volume;
   (f) said lamp bulb being disposed approximately coaxially with the housing, and being spaced apart from said annular interior surface so as to define an annular portion of said space volume therebetween; and,
   (g) means for supporting the bristled ends of said toothbrushes at spaced apart locations surrounding said lamp within the annular portion of said space volume;
   (h) said means defining the annular interior surface comprising a cylindrical cup removably supported within the housing in surrounding coaxial relationship with the lamp bulb, the removable cup having top and bottom ends; and, (i) said means for supporting the bristled ends of said toothbrushes comprising said cup, and an inwardly extending annular ledge formed adjacent the bottom end of the cup for abutting the bristled ends of said toothbrushes.

3. The germicidal toothbrush holder of claim 1, wherein the detachable lid of the housing has a plurality of openings therein at spaced apart locations in an annular array which registers with said inwardly extending annular ledges and corresponds with the openings in said second annular ledge, the lid openings being sized to accommodate the insertion of bristled ends of said toothbrushes therethrough respectively, with the vertical spacing between the detachable housing lid and the first annular ledge being substantially less than the length of the toothbrushes whereby the proximal end portions of the handles of the toothbrushes protrude upwardly through the openings in the detachable lid, and with said vertical spacing being sufficient to include substantial portions of the toothbrush handles within the upper space volume for irradiation by said lamp.

4. The germicidal toothbrush holder of claim 2, wherein at least the major portion of the annular interior surface defined by the cylindrical cup is comprised of material which is highly reflective of ultraviolet light in the 200 to 300 nanometer wavelength spectrum.

5. The germicidal toothbrush holder of claim 3, wherein the detachable lid of the housing has a bottom surface exposed to said interior space volume, which bottom surface is comprised of material which is highly reflective of ultraviolet light in the 200 to 300 nanometer wavelength spectrum.

6. The germicidal toothbrush holder of claim 2, wherein the means for supporting the bristled ends of said toothbrushes further comprises means defining a second inwardly extending annular ledge supported within the cup at a location spaced above said first annular ledge, said second annular ledge having a plurality of openings therein disposed at spaced apart locations through which the bristled ends of said toothbrushes may be inserted respectively.

7. The germicidal toothbrush holder of claim 1, wherein the means for mounting the lamp operatively comprises a lamp socket mounted centrally to the bottom wall of the housing, and means communicating through a wall of the housing to the lamp socket for supplying electrical energy thereto at a low power level, not substantially in excess of that required to operate a four watt ultraviolet light bulb.

8. The germicidal toothbrush holder of claim 1, wherein the wavelength spectrum of the electric lamp includes wavelengths in the visible spectrum; and, wherein at least a substantial portion of the side wall of the cylindrical housing disposed below said upper space volume is absorbant of ultraviolet light, but translucent to visible light.

9. The germicidal toothbrush holder of claim 8, wherein the side wall of the housing is comprised of polypropylene plastic.

* * * * *